United States Patent [19]
Swenson et al.

[11] Patent Number: 5,666,963
[45] Date of Patent: Sep. 16, 1997

[54] MOVING-STIMULUS THERMAL SENSITIVITY TESTING DEVICE

[75] Inventors: Michael R. Swenson; Robert Healey, both of San Diego, Calif.

[73] Assignee: The Regents of the University of California, Oakland, Calif.

[21] Appl. No.: 426,386

[22] Filed: Apr. 21, 1995

[51] Int. Cl.⁶ ............................................. A61B 5/00
[52] U.S. Cl. ............................................. 128/742; 128/744
[58] Field of Search ................................. 128/742, 744; 601/18, 19, 112, 113, 118–120, 129, 131

[56] References Cited

U.S. PATENT DOCUMENTS

| | | | |
|---|---|---|---|
| 1,947,042 | 2/1934 | Glennan | 601/19 |
| 4,026,275 | 5/1977 | Jablecki | 128/742 |

FOREIGN PATENT DOCUMENTS 0026880 of 1906 United Kingdom ................. 601/19

*Primary Examiner*—Max Hindenburg
*Attorney, Agent, or Firm*—Townsend and Townsend and Crew LLP

[57] ABSTRACT

Losses in nerve sensation are detected, and the affected nerves identified, by a hand-held device which is drawn, and preferably rolled, over the surface of a subject's skin. The surface on the device which contacts the subject's skin is made of a high thermal conductivity material, and when the device is at room temperature, a cooling sensation is experienced by the subject except in those regions where nerve sensation is abnormally low. The device is thus useful in delineating the regions of nerve sensation loss, as a useful step in monitoring certain disease conditions. The device also finds utility as a tool for cold massage.

4 Claims, 4 Drawing Sheets

MOVING-STIMULUS THERMAL SENSITIVITY TESTING DEVICE

This invention resides in the field of medical techniques and devices for the detection of epidermal nerve disorders.

BACKGROUND OF THE INVENTION

The small fibers within nerves are called "axons," and their function is to transmit bioelectric signals known as "action potentials" to various parts of the body either as a warning mechanism or to induce a particular action. Motor axons carry action potentials to the muscles for control of movement, while sensory axons carry action potentials from the skin and other sensitive structures to the central nervous system for sensory perception. The area of skin containing axons from a single nerve is termed a "dermatome."

Nerve injuries from localized causes such as trauma, lacerations, or crushing or entrapment of the nerve are readily detected by determining loss of sensation at the dermatome. The determination is commonly performed by drawing a wisp of cotton or a simple pin across the skin surface to serve as a stimulus. By noting changes in the sensations felt by the patient under the moving stimulus, the physician can ascertain the shape and location of the area of sensory loss and compare these to the known nerve anatomy to determine which nerves have been injured. Unfortunately, the sensation differentials are either so small that they are difficult to detect, or if detectable are irritating to the patient. Furthermore, they are so narrowly localized that a prolonged process is sometimes required for a full and reliable determination. A device specifically designed for this type of testing is the Wartenberg wheel, which is a small wheel with sharp protruding pins. The use of this device is not currently favored, however, due to its risk of HIV, hepatitis or other infectious transmissions.

In addition to localized causes, nerve injury can result from medical disorders which affect the nerves in general, a condition known as polyneuropathy. Examples of these disorders are diabetes, acute and chronic Guillain-Barré syndrome, toxic neuropathies and neuropathies associated with collagen-vascular diseases such as systemic lupus erythematosis and rheumatoid arthritis. In polyneuropathy, the nerves which are initially affected are those with the longest nerve fibers, and thus the first loss of sensation appears distally in the feet, ankles, hands and wrists. As the condition worsens, the boundaries of sensory loss travel slowly upward (inward from the extremities). With successful treatment of the condition, boundaries retreat back toward the extremities. Thus, by monitoring the location of these boundaries, the physician can monitor and plot the progression of the condition or the patient's response to treatment. The known methods noted above present the same limitations in polyneuropathy as in localized causes of nerve injury. Other, more elaborate devices employ the use of temperature-controlled water pumped to a touch pad, but these are applicable only to detections at finger and toe tips, and entail substantial cost.

The need to monitor a patient's response to treatment by a reliable yet inexpensive method is of growing importance as health care increasingly adopts principles of managed care and cost containment. The mapping of injured sensory dermatomes is one means of serving this need.

SUMMARY OF THE INVENTION

This invention resides in a thermal sensitivity testing device and its use as a moving stimulus for determining the boundaries of skin regions suffering losses in sensation. By virtue of its construction and thermal properties, the device is also capable of serving as a massage aid for cold massage therapy.

The device is a smooth-surfaced, hand-held device whose surface which is placed in contact with the patient's skin is formed of a material of high thermal conductivity. Such materials feel cool to the touch, even when at ambient temperature, due to the small temperature differential between ambient temperature and the patient's body temperature, the high thermal conductivity rapidly drawing heat from the patient's body, thereby creating the sensation of coolness. In preferred embodiments of the invention, the device is a body of revolution, such as a sphere, an ellipsoid or a cylinder, and is rollably mounted to a handle so that the high thermal conductivity material can be rolled over the skin surface. The handle is preferably of a low thermal conductivity material to minimize any risk of heat transmission to the device from the operator's hand. In use, the device is held by the operator and rolled over the skin surface applying little or no pressure while noting the patient's observations of a cool sensation or the lack thereof.

For embodiments of the invention constructed as rollers, the device can be used as a massage aid by applying moderate to heavy pressure and using the device over regions where cold massage is needed.

These and other features, objects and advantages of the invention are described in further detail below.

DETAILED DESCRIPTION OF THE INVENTION AND PREFERRED EMBODIMENTS

Figure 1:
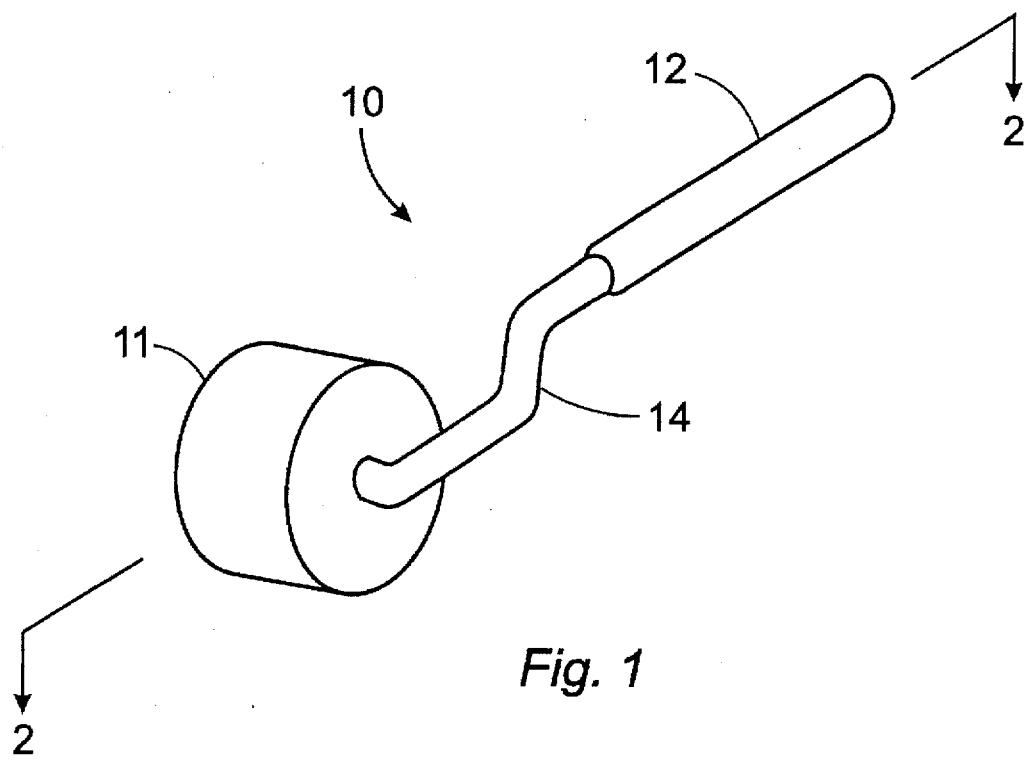
FIG. 1 is a perspective view of a moving-stimulus thermal sensitivity testing device in accordance with the present invention.

While the device of the invention, its method of use and its range of application are all generic in scope, encompassing a variety of possible embodiments, the invention will be best understood by reference to a specific example, as shown in the drawings.

Figure 2:
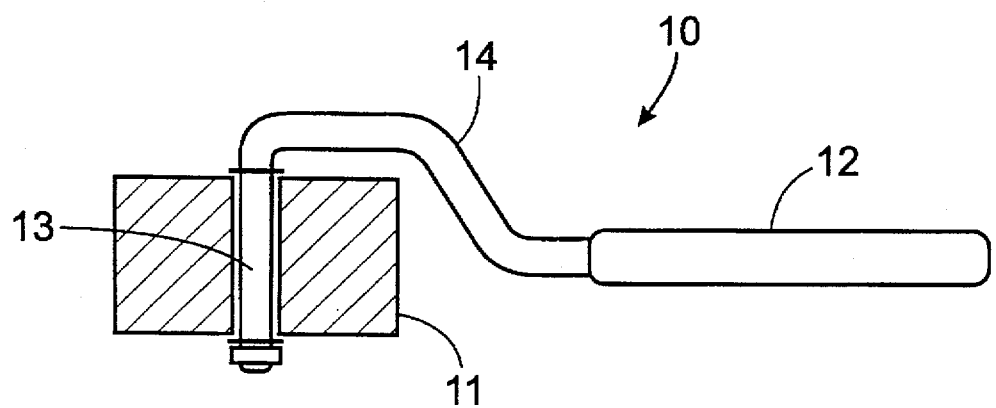
FIG. 2 is a horizontal cross section view of the device of FIG. 1, taken along the line 2—2 thereof.

FIGS. 1 and 2 show the device 10 in perspective and cross section views, respectively. The device consists of a cylindrical roller 11 mounted to a handle 12 through a pin 13 which passes through the axis of the roller and around which the roller rotates. The pin 13 is in turn connected to the handle 12 through a connecting segment 14, which places the pin and the handle at a right angle relative to each other.

The thermal conductivity of the material at the surface of the roller 11 is at least about 0.200 g-cal/(sec)(cm$^2$)(°C./cm), which may be expressed in English units as at least about 1.12×10$^{-3}$ Btu/(sec)(in$^2$)(°F./inch). Preferably, the thermal conductivity of this material is at least about 0.400 g-cal/(sec)(cm²)(°C./cm) or, in English units, at least about 2.24×10⁻³ Btu/(sec)(in²)(°F./inch). Examples of suitable materials are metallic materials such as aluminum, aluminum-based alloys, silver, silver-based alloys, copper, and copperbased alloys. The entire roller can be constructed of this material, or the roller can be clad or ensheathed in this material.

As mentioned above, alternatives to the cylindrical roller shown are spherical rollers, ellipsoid rollers, or any other shape which will smoothly roll over the skin surface. The roller can also be replaced by a nonrolling structural element, such as a flat or other smooth-surfaced element either rigidly mounted to the handle or mounted in a pivotal manner permitting pivoting of the element to follow the contour of the skin. Rollers are preferred since upon being drawn across the skin they entail essentially no friction which might interfere with perceptions of coolness.

The dimensions of the roller 11 are not critical, and will generally be selected to provide full contact with the skin across the width of the roller without applying pressure. In a presently preferred construction, the roller has a diameter of about 1.5 inch (3.8 cm) and a width of about 1 inch (2.5 cm).

The handle 12 preferably has a surface of a material which has a conductivity of less than about 0.100 g-cal/(sec)(cm²)(°C./cm) or, expressed in English units, at least about 0.56×10⁻³ Btu/(sec)(in²)(°F./inch). More preferably, the handle surface has a conductivity which is lower than that of the roller by at least about 0.350 g-cal/(sec)(cm²)(°C./cm) or, expressed in English units, at least about 1.96×10⁻³ Btu/(sec)(in²)(°F./inch). Examples of materials which would be suitable for the handle surface are stainless steel, carbon steel, wood, and plastic. This material can constitute either the entire handle or a sleeve encasing the handle.

The device can be used at any convenient temperature which is lower than the body temperature of the patient. The device can be conveniently used, for example, at room temperature with effective results. Room temperature for these purposes is defined as a temperature approximately in the range of 18°–25° C., or preferably 22°–24° C., a temperature range typically maintained in clinics. With a typical patient skin temperature of about 30°–33° C., this results in a temperature differential between the skin surface and the device surface of about 5°–15° C.

For use as a moving stimulus to detect regions of sensory loss, the device shown in FIGS. 1 and 2 is hand-held by the physician or operator, and is rolled over the skin surface of a human patient, starting from a zone of normal sensation and moving toward and over a symptomatic area. While this is occurring, the patient is asked to notify the operator when the sensation changes, the location of a change being marked by the operator as the location of a boundary. By making several passes with the device over neighboring skin regions, all boundaries of the region of reduced sensation are delineated. The operator can plot these boundaries on the skin surface with a marking pen and then record the marked areas by a photograph or sketch.

Figure 3:
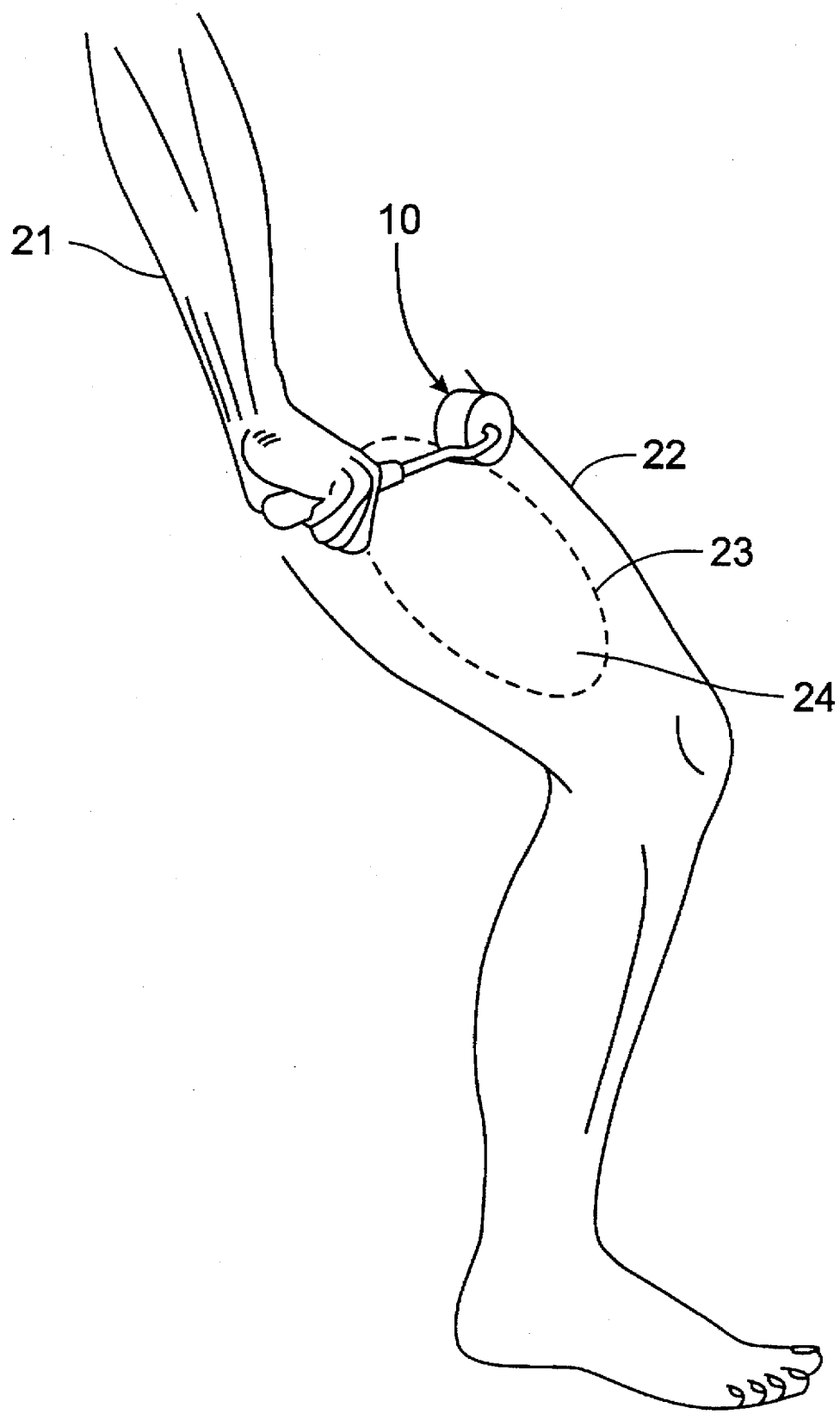
FIG. 3 depicts the device of FIGS. 1 and 2 in use mapping the distribution of the lateral femoral cutaneous nerve.

One illustration of the use of the device is shown in FIG. 3. Here the device 10 is hand-held by the operator 21 and applied to the outer surface of a patient's thigh 22. With the assistance of the patient, the device is used to delineate the boundary 23 of the dermatome 24 of the lateral femoral cutaneous nerve.

Figure 4:
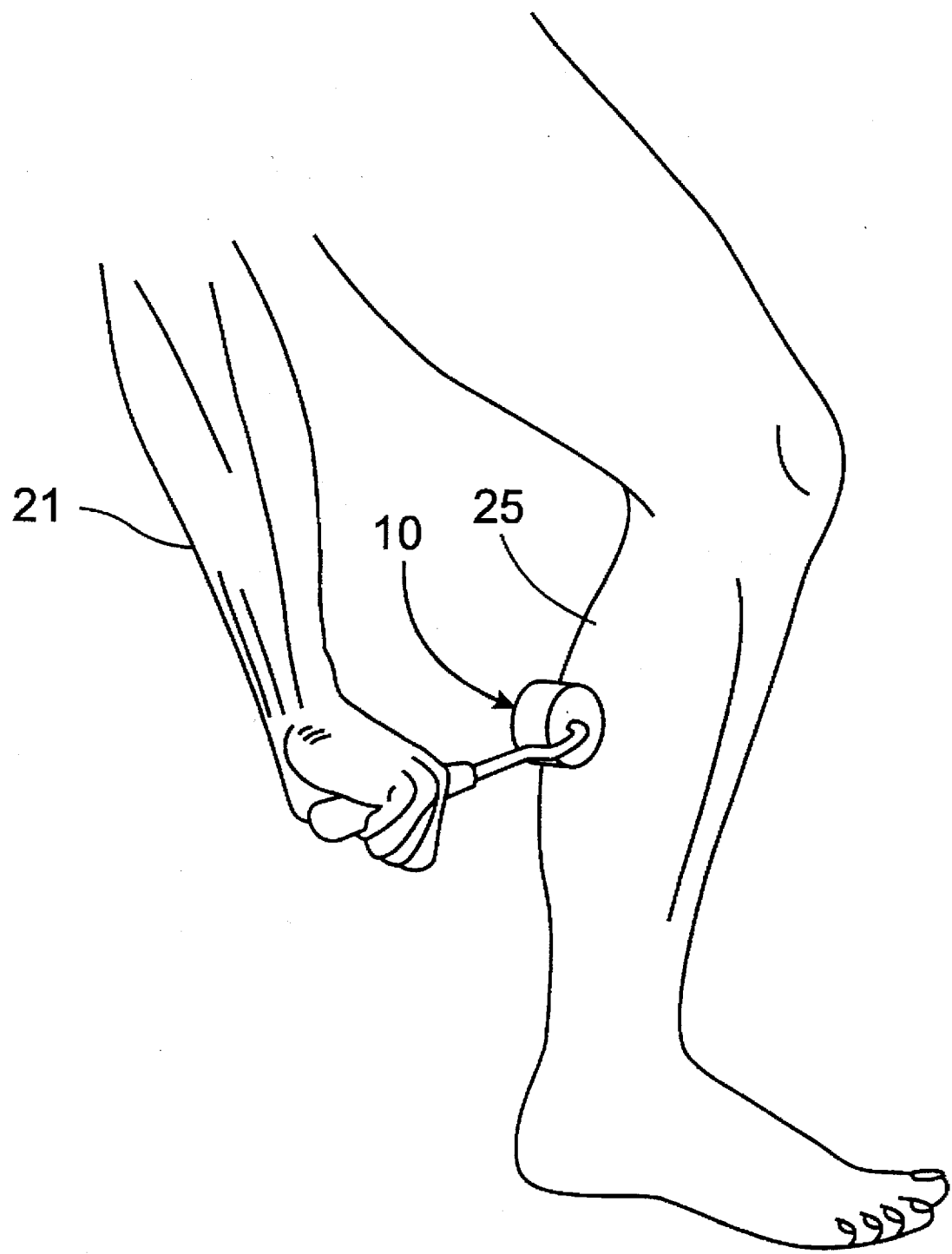
FIG. 4 depicts the device of FIGS. 1 and 2 in use monitoring the progress of a polyneuropathy.

Another illustration appears in FIG. 4. Here the device 10 is used to monitor a polyneuropathy, and is being rolled downward along the calf region of the patient's lower leg 25 to determine the location at which sensation first diminishes.

Figure 6:
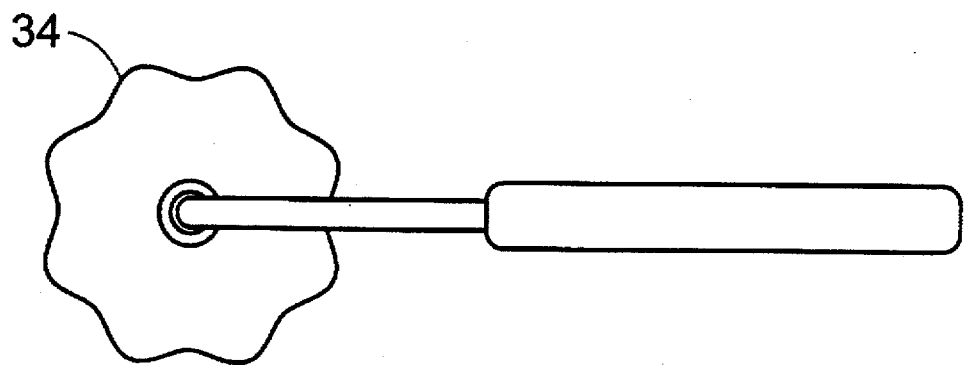
FIG. 6 is a side view of a still further device in accordance with the invention, in which the roller surface is lobed to provide extra stimulus as a massage aid.
Figure 5:
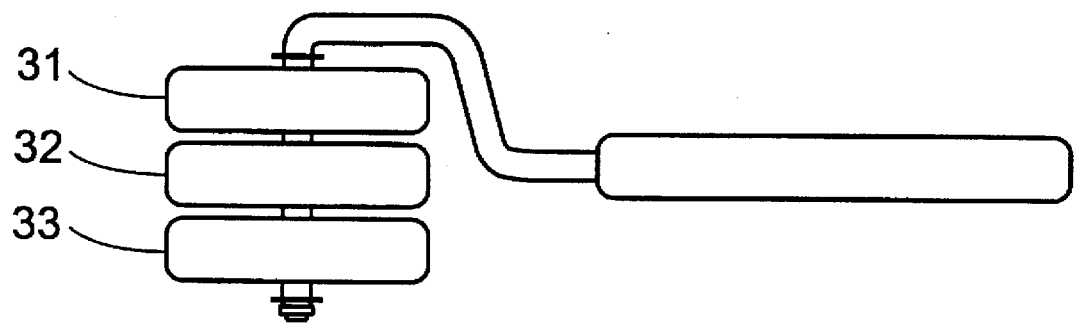
FIG. 5 is a top view of a three-roller device in accordance with the invention.

For use in massage therapy, the device is particularly useful in regions of the neck, shoulder and paraspinal region for patients suffering from pain in those regions. Conventional massage techniques can be used, the device enhancing those techniques by virtue of its cooling effect. Depending on the location and contours of the region where massage is applied and the condition of the underlying muscles or ligaments, the device may be constructed with one roller as shown in FIGS. 1 and 2, or with two, three or more rollers, arranged either coaxially or with displaced parallel axes. A three-roller version of the device is shown in FIG. 5, in which the rollers 31, 32, 33 are coaxial. A spherical or ellipsoid roller will generally be more effective as a massage aid than a cylindrical roller. Furthermore, the surface of the roller may be smooth or it may have bumps preformed in it for deeper muscle penetration. FIG. 6 illustrates a lobed-surface roller containing regularly spaced lobes 34.

The foregoing is offered primarily for purposes of illustration. It will be readily apparent to those skilled in the art that the dimensions, materials, operating methods and conditions and other parameters of the device described herein and its methods of use may be further modified or substituted in various ways without departing from the spirit and scope of the invention.

What is claimed is:

1. A method for testing a patient's skin surface to detect regions of sensory loss, said method comprising:

(a) manually drawing across said skin surface a smooth-surfaced device whose surface is formed of a material having a thermal conductivity of at least about 0.200 g-cal/(sec)(cm²)(°C./cm) while maintaining continuous contact between said skin surface and said smooth-surfaced device; and (b) differentiating sensate regions of said skin surface at which said skin experiences a cooling sensation upon contact with said smooth-surfaced device from relatively insensate regions at which substantially less of a cooling sensation is experienced, and thereby delineating the boundaries of said relatively insensate regions.

2. A method in accordance with claim 1 in which (a) further comprises holding said smooth-surfaced device by a handle having a surface formed of a material having a thermal conductivity of less than about 0.100 g-cal/(sec)(cm²)(°C./cm).

3. A method in accordance with claim 1 in which said smooth-surfaced device is a roller whose surface is formed of a material having a thermal conductivity of at least about 0.400 g-cal/(sec)(cm²)(°C./cm), and (a) comprises rolling said roller across said skin surface.

4. A method in accordance with claim 1 in which said (a) is conducted while said surface of said device is at a temperature of approximately 22°–24° C.

* * * * *